United States Patent [19]

Waldstein

[11] 3,950,541

[45] Apr. 13, 1976

[54] AQUEOUS COMPOSITIONS CONTAINING QUATERNARY AMMONIUM SALTS FOR TREATMENT OF RECTAL ITCHING AND LESSENING OF IRRITATION AND SWELLING OF PROLAPSED AND OF IRRITATED AND SWOLLEN EXTERNAL HEMORRHOIDS

[76] Inventor: David A. Waldstein, 622 Bergen Ave., Jersey City, N.J. 07304

[22] Filed: Nov. 1, 1973

[21] Appl. No.: 411,730

Related U.S. Application Data

[63] Continuation-in-part of Ser. No. 182,201, Sept. 20, 1971, abandoned, which is a continuation-in-part of Ser. No. 660,906, Aug. 16, 1967, abandoned.

[52] U.S. Cl. .............................................. 424/329
[51] Int. Cl.$^2$.................................... A61K 31/14
[58] Field of Search ................................... 424/329

[56] References Cited
UNITED STATES PATENTS 3,026,169   3/1962   Eskridge ......................... 260/567.6

OTHER PUBLICATIONS

Grosicki et al., — Handbook on Non-Prescription Drugs, pp. 72–76, (1967).

Collins, — Family Medical Encyclopedia, Ed. G. Sommerville, 1952, pp. 530–531.

Schwartz & Perry, Surface Active Agents, Vol. 1, pp. 151–153, (1949).

*Primary Examiner*—Leonard Schenkman
*Attorney, Agent, or Firm*—Kirschstein, Kirschstein, Ottinger & Frank

[57] ABSTRACT

Aqueous compositions containing quaternary ammonium polyalkoxy(C2–3) alkyl(C10–25) alkyl(C1–6) salts and a method of using such compositions for relieving rectal itching and lessening irritation and swelling of prolapsed and of irritated and swollen external hemorrhoids by topical application.

2 Claims, No Drawings

AQUEOUS COMPOSITIONS CONTAINING QUATERNARY AMMONIUM SALTS FOR TREATMENT OF RECTAL ITCHING AND LESSENING OF IRRITATION AND SWELLING OF PROLAPSED AND OF IRRITATED AND SWOLLEN EXTERNAL HEMORRHOIDS

CROSS-REFERENCE TO RELATED APPLICATIONS

The application is a continuation-in-part of application Ser. No. 182,201, filed Sept. 20, 1971, which is a continuation-in-part of Ser. No. 660,906, filed Aug. 16, 1967, both now abandoned.

BACKGROUND OF THE INVENTION

1. Field of the Invention

An aqueous composition containing a quaternary ammonium polyalkoxy(C2-3) alkyl(C10-25) alkyl(-C1-6) salt and a method of topically applying such a composition to a person's rectum for relieving itching and for lessening irritation and swelling of external hemorrhoids.

2. Description of the Prior Art

Heretofore, rectal itching has been alleviated to some extent by laving and cleansing affected part with water, and soap and water solutions with or without rectal irrigation. It also has been proposed to use various prescribed medicated suppositories and salves including, for example, cortisone, and to hypodermically inject prescribed medication into hemorrhoids. In addition, many proprietary remedies have been sold over-the-counter. However, none of the foregoing treatments and materials have proven to be fully acceptable because of failure to satisfactorily alleviate the symptoms or correct the cause or because of the inability of the sufferer to practice the suggested regime on himself.

SUMMARY OF THE INVENTION

Purposes of the Invention

It is an object of the invention to provide an aqueous composition containing a quaternary ammonium polyalkoxy(C2-3) alkyl(C10-25) alkyl(C1-6) salt from the group consisting of quaternary ammonium bis polyalkoxy(C2-3) monoalkyl(C10-25) monoalkyl(C1-6) salts, quaternary ammonium mono polyalkoxy(C2-3) dialkyl(C10-25) monoalkyl(C1-6) salts, and quaternary ammonium mono polyalkoxy(C2-3) monoalkyl(C10-25) dialkyl(C1-6) salts, and a method of topically applying such a composition to a person's rectum for relieving itching and for lessening irritation and swelling of external hemorrhoids.

It is another object of the invention to provide a novel method of using such composition for relieving rectal itching and lessening irritation and swelling of prolapsed and of irritated and swollen external hemorrhoids.

Other objects of the invention in part will be obvious and in part will be pointed out hereinafter.

Brief Description of the Invention

The foregoing objects of the invention are obtained by the use in water of a quaternary ammonium polyalkoxy(C2-3) alkyl(C10-25) alkyl(C1-6) salt from the group consisting of quaternary ammonium bis polyalkoxy(C2-3) monoalkyl(C10-25) monoalkyl(C1-6) salts, quaternary ammonium mono polyalkoxy(C2-3) dialkyl(C10-25) monoalkyl(C1-6) salts, and quaternary ammonium mono polyalkoxy(C2-3) monoalkyl(C10-25) dialkyl(C1-6) salts where the quaternary ammonium bis polyalkoxy(C2-3) monoalkyl(C10-25) monoalkyl(C1-6) salts are of the formula

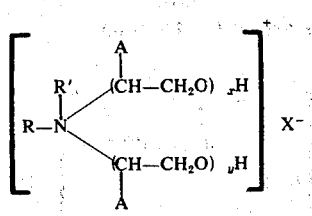

where R is a saturated or unsaturated fatty alkyl having from 10 to 25 carbon atoms, each A is hydrogen or methyl, R' is a lower alkyl having from 1 to 6 carbon atoms, $x$ is at least 2, $y$ is at least 2, $x + y$ is from 5 to 60 and X is selected from the group consisting of chlorides, iodides, bromides, sulfonates and sulfates; where the quaternary ammonium monopolyalkoxy(C2-3) dialkyl(C10-25) monoalkyl(C1-6) salts are of the formula

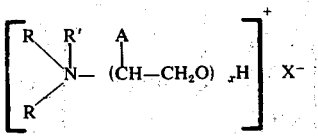

where each R is a saturated or unsaturated fatty alkyl having from 10 to 25 carbon atoms, A is hydrogen or methyl, R' is a lower alkyl having from 1 to 6 carbon atoms, $x$ is from 5 to 60 and X is selected from the group consisting of chlorides, iodides, bromides, sulfonates and sulfates; and where the quaternary ammonium monopolyalkoxy(C2-3) monoalkyl(C10-25) dialkyl(C1-6) salts are of the formula

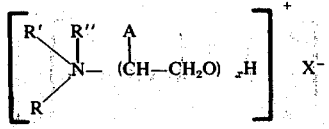

where R is a saturated or unsaturated fatty allyl having from 10 to 25 carbon atoms, A is hydrogen or methyl, R' and R'' are each a lower alkyl having from 1 to 6 carbon atoms, $x$ is from 5 to 60 and X is selected from the group consisting of chlorides, iodides, bromides, sulfonates and sulfates.

A quaternary ammonium salt as aforesaid in water is particularly useful for topical application to a rectal area affected by itching or for obtaining symptomatic relief of irritation and swelling of prolapsed and of irritated and swollen external hemorrhoids.

DESCRIPTION OF THE PREFERRED EMBODIMENTS

The method of the invention is carried out by topically applying to an affected area an aqueous solution containing a quaternary ammonium polyalkoxy(C2-3)

alkyl(C10–25) alkyl(C1–6) salt from the group consisting of quaternary ammonium bis polyalkoxy(C2–3) monoalkyl(C10–25) monoalkyl(C1–6) salts, quaternary ammonium mono polyalkoxy(C2–3) dialkyl(C10–25) monoalkyl(C1–6) salts, and quaternary ammonium mono polyalkoxy(C2–3) monoalkyl(C10–25) dialkyl(C1–6) salts where the quaternary ammonium bis polyalkoxy(C2–3) monoalkyl(C10–25) monoalkyl(C1–6) salts are of the formula

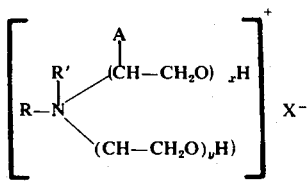

where R is a saturated or unsaturated fatty alkyl having from 10 to 25 carbon atoms, each A is hydrogen or methyl, R' is a lower alkyl having from 1 to 6 carbon atoms, $x$ is at least 2, $y$ is at least 2, $x + y$ is from 5 to 60 and X is selected from the group consisting of chlorides, iodides, bromides, sulfonates and sulfates; where the quaternary ammonium mono polyalkoxy(C2–3) dialkyl(C10–25) monoalkyl(C1–6) salts are of the formula

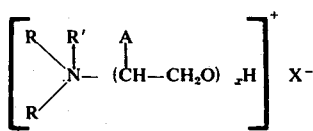

where each R is a saturated or unsaturated fatty alkyl having from 10 to 25 carbon atoms, A is hydrogen or methyl, R' is a lower alkyl having from 1 to 6 carbon atoms, $x$ is from 5 to 60 and X is selected from the group consisting of chlorides, iodides, bromides, sulfonates and sulfates; and where the quaternary ammonium monopolyalkoxy(C2–3) monoalkyl(10–25) dialkyl(C1–6) salts are of the formula

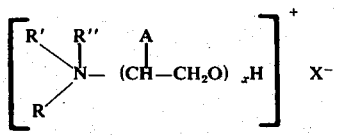

where R is a saturated or unsaturated fatty alkyl having from 10 to 24 carbon atoms, A is hydrogen or methyl, R' and R'' are each a lower alkyl having from 1 to 6 carbon atoms, $x$ is from 5 to 60 and X is selected from the group consisting of chlorides, iodides, bromides, sulfonates and sulfates. Such quaternary ammonium salts is applied either by itself or in a pharmacologically acceptable carrier.

The fatty alkyl group identified in the above formulae as R is a saturated alkyl such as palmityl, stearyl, myristyl, behenyl, coconut oil alkyls, and the like, as well as alkenyl such as oleyl, linoleyl, linolenyl, and the like. Preferably, said fatty alkyl group has from 12 to 22 carbon atoms.

The term "lower alkyl" as used herein denotes an alkyl radical having from 1 to 6 carbon atoms such as methyl, ethyl, propyl, n-butyl, secondary butyl, amyl, hexyl, and the substituted radical benzyl.

The term $x + y$ in the formula for the quaternary ammonium bispolyalkoxy(C2–3) monoalkyl(C10–25) monoalkyl(C1–6) salts indicates the cumulative value for the alkoxy substituents, being in the range of 5 to 60 as indicated above. In the same bispolyalkoxy salts the $x$ and $y$ each should range from 2 to 30. In the preferred aspect of the invention the value of $x + y$ is from 5 to 45, and in no event is the value of either $x$ or $y$ less than 2 for the bispolyalkoxy salts. In all instances the degree of polyalkoxylation indicated for the bis(polyalkoxy) quaternary ammonium salts is approximately uniformly divided between the two polyalkoxy groups or, reverting to the $x$ and $y$ terminology, $x$ is approximately equal to $y$. There must always be at least 5 alkoxy substituents attached directly to the nitrogen atom for the quaternary ammonium monopolyalkoxy salts. $x$ for the quaternary ammonium monopolyalkoxy salts, as indicated above, ranges from 5 to 60.

The term X denotes the anionic radical of the compound R'X or R''X which is used in the quaternization of a tertiary amine to form the quaternary ammonium salt of the present invention. X can be chloride, iodine, bromine, a sulfonate, a sulfate and the like. Typical salts for quaternization of the tertiary amines are dimethyl sulfate, diethyl sulfate, benzyl chloride, methyl chloride, ethyl chloride, butyl chloride, hexyl chloride, methyl iodide, ethyl bromide, propyl bromide, n-butyl bromide, secondary butyl bromide, hexyl bromide, and p-toluene sulfonate.

The aforesaid quaternary ammonium polyalkoxy(C2–3) alkyl(C10–25) alkyl(C1–6) salts useful in carrying out the invention are commercially available products. They can be prepared by methods well known in the art. For example, they can be prepared by the polyalkoxylation of a fatty alkyl amine(C10–25) and the quaternization of the resulting product exemplified by the following reaction schemes. In these schemes the polyalkoxylation is shown as being performed by polyethoxylation and it is to be understood that the same scheme is applicable to polypropoxylation, propylene oxide being substituted for ethylene oxide.

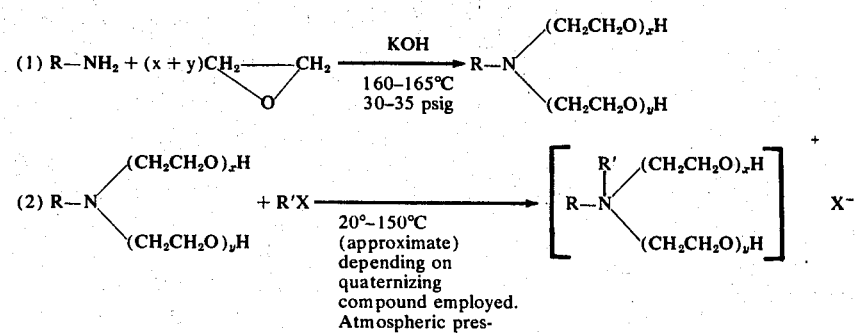

sure to triple atmospheric pressure depending on quaternizing compound employed.

The aforesaid reactions are typically employed to prepare quaternary ammonium bispolyalkoxy(C2-3) monoalkyl(C10-25) monoalkyl(C1-6) salts.

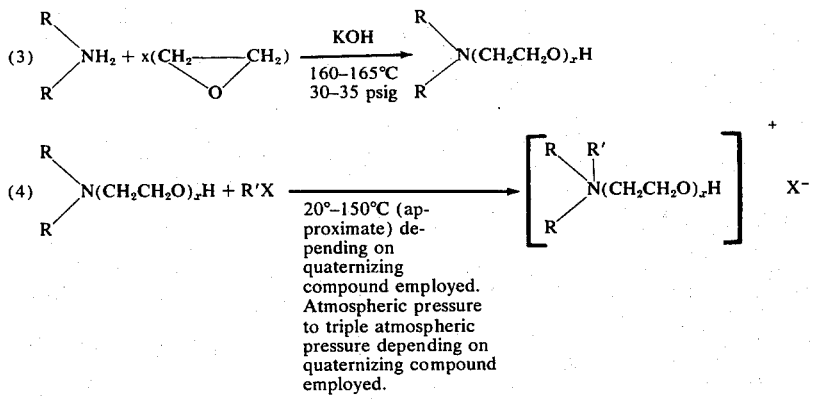

The aforesaid reactions are typically employed to prepare quaternary ammonium monopolyalkoxy(C2-3) dialkyl(C10-25) monoalkyl(C1-6) salts.

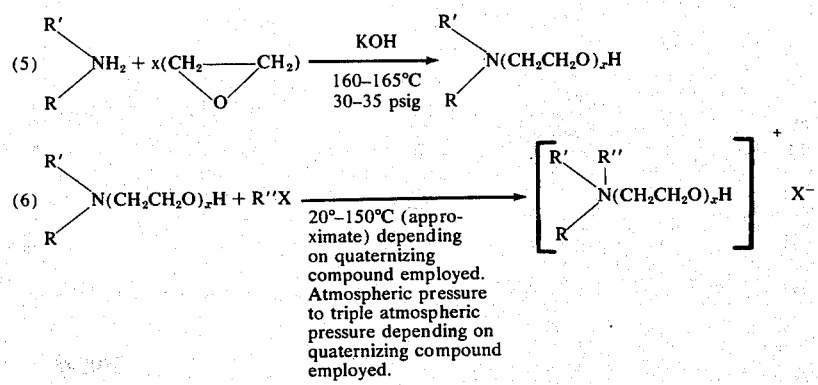

The aforesaid reactions are typically employed to prepare monopolyalkoxy(C2-3) monoalkyl(C10-25) dialkyl(C1-6) salts.

Reaction (1) is carried out by placing the alkyl amine, e.g. stearyl amine, in a closed reactor with an agitator under a pressure of two atmospheres in the presence of potassium hydroxide acting as a catalyst and maintaining the termperature between 160°C and 165°C. Ethylene oxide is pumped in a steady flow into the reactor and the pressure gauge on the reactor is observed. The flow is maintained at a rate such that the pressure remains constant at two atmospheres, indicating that the desired absorption (reaction) of ethylene oxide is taking place. The degree of polyethoxylation is determined by weighing the amount of ethylene oxide introduced into the reactor. From 5 to 60 mols of ethylene oxide will be absorbed in reaction (1) in from 2 to 6 hours. At the end of about 3 hours about 25 mols of ethylene oxide are absorbed (reacted). Reactions (3) and (5) are carried out in exactly the same manner as reaction (1).

Reactions (2), (4) and (6) are carried out at atmospheric pressure by mixing a quaternizing salt with the tertiary amine formed by reaction (1), (3) or (5) for 1 to 5 hours. The following examples set forth in detail methods of preparing compounds representative of compounds of the present invention.

For the tallow bispolyethoxy (25 mols ethylene oxide) ethyl quaternary ammonium slufate, a primary tallow amine is reacted pursuant to reaction (1) with approximately 25 molar equivalents of ethylene oxide in the presence of 0.2 to 0.4% by weight of potassium hodroxide based upon the weight of the hydrogenated primary tallow amine. This reaction is carried out for 3 hours, the tertiary amine product being sampled from time to time to determine the degree of polyethoxylation and, once the time is known, the reaction being repeated for the same length of time and the same reaction conditions for future production. Pursuant to reaction (2) to 1360 grams of the bis(polyethyoxylated) tertiary amine secured from reaction (1) containing 25 mols of ethylene oxide and which is maintained at a temperature of about 85°C, there is added slowly with vigorous agitation 154 grams of diethyl sulfate. The reaction is exothermic. The temperature will rise to about 110°C. After the alkalinity drops to about 3 to 5 milligrams KOH the reaction is completed. The reaction is carried out at a suitable pressure which, in this instance, may be atmospheric and the desired reaction is completed in from about 1 to 3 hours. The reaction product obtained is a tallow bis(polyethoxylated-25 mols ethylene oxide) ethyl quaternary ammonium sulfate.

The same process as outlined above is likewise employed to make a ditallow mono(polyalkoxy) monoethyl quaternary ammonium sulfate, and a monotallow(polyalkoxy) ethyl methyl quaternary ammonium sulfate, the only variation being the change in the starting amines which are respectively a ditallow secondary amine and a tallow ethyl secondary amine.

To manufacture other fatty alkyl quaternary ammonium salts different starting amines are employed in which the fatty alkyl constituent of the starting amine corresponds to the fatty alkyl constituent of the quaternary ammonium salt. To prepare quaternary ammonium salts having different mono lower alkyl constituents, quaternizing salts having corresponding lower alkyl constituents are employed and, in a similar manner, if di lower alkyl quaternary ammonium salts are to be prepared, one of the lower alkyl constituents is incorporated in the starting amine which is secondary and includes both the higher and the lower alkyl constituents, the other alkyl constituent being supplied by the quaternizing salt.

If it is desired to have a lower molar equivalent of ethylene oxide the polyethoxylation step is carried out for a shorter period of time, e.g. for 15 mols of ethylene oxide in the neighborhood of 1½ hr. If a higher molar equivalent of ethylene oxide is desired to be incorporated the polyethoxylation step is carried out for a longer period of time, e.g. in the neighborhood of 4½ hr. for a 45 molar equivalent of ethylene oxide and 6 hrs. for incorporation of 60 molar equivalents of ethylene oxide.

For the polypropoxylated quaternary ammonium salts the alkoxylation is carried out with the use of propylene oxide instead of ethylene oxide.

The reactions set forth above employing the proper higher and lower alkyl groups, and employing the proper alkoxy compound, and the proper quaternizing salts are used to produce the following quaternary ammonium salts all of which are useful in practicing the present invention either per se or in combination with the phamacologically acceptable carrier, and all can be employed, i.e. the salt per se and the compositions including the salts, in such a carrier for treatments pursuant to the present invention.

In all instances the degree of polyalkoxylation indicated for the quaternary ammonium bispolyalkoxy alkyl alkyl salts is approximately uniformly divided between the two polyalkoxy groups or, reverting to the $x, y$ terminology, $x$ is approximately equal to $y$.

Table I monostearyl bis(polyethoxy) monomethyl quaternary ammonium chloride, iodide, bromide, sulfonate and sulfate (with 5, 15, 25, 45 or 60 mols ethylene oxide);
monotallow bis(polyethoxy) monomethyl quaternary ammonium chloride, iodide, bromide, sulfonate and sulfate (with 5, 15, 25, 45 or 60 mols ethylene oxide);
monolauryl bis(polyethoxy) monomethyl quaternary ammonium chloride, iodide, bromide, sulfonate and sulfate (with 5, 15, 25, 45 or 60 mols ethylene oxide);
monococo bis(polyethoxy) monomethyl quaternary ammonium chloride, iodide, bromide, sulfonate and sulfate (with 5, 15, 25, 45 or 60 mols ethylene oxide);
monomyristyl bis(polyethoxy) monomethyl quaternary ammonium chloride, iodide, bromide, sulfonate and sulfate (with 5, 15, 25, 45 or 60 mols ethylene oxide);
monobehenyl bis(polyethoxy) monomethyl quaternary ammonium chloride, iodide, bromide, sulfonate and sulfate (with 5, 15, 25, 45 or 60 mols ethylene oxide);
monopalmityl bis(polyethoxy) monomethyl quaternary ammonium chloride, iodide, bromide, sulfonate and sulfate (with 5, 15, 25, 45 or 60 mols ethylene oxide);
monosoya bis(polyethoxy) monomethyl quaternary ammonium chloride, iodide, bromide, sulfonate and sulfate (with 5, 15, 25, 45 or 60 mols ethylene oxide);
monooleyl bis(polyethoxy) monomethyl quaternary ammonium chloride, iodide, bromide, sulfonate and sulfate (with 5, 15, 25, 45 or 60 mols ethylene oxide);
monostearyl bis(polyethoxy) monoethyl quaternary ammonium chloride, iodide, bromide, sulfonate and sulfate (with 5, 15, 25, 45 or 60 mols ethylene oxide);
monotallow bis(polyethoxy) monoethyl quaternary ammonium chloride, iodide, bromide, sulfonate and sulfate (with 5, 15, 25, 45 or 60 mols ethylene oxide);
monolauryl bis(polyethoxy) monoethyl quaternary ammonium chloride, iodide, bromide, sulfonate and sulfate (with 5, 15, 25, 45 or 60 mols ethylene oxide);
monococo bis(polyethoxy) monoethyl quaternary ammonium chloride, iodide, bromide, sulfonate and sulfate (with 5, 15, 25, 45 or 60 mols ethylene oxide);
monomyristyl bis(polyethoxy) monoethyl quaternary ammonium chloride, iodide, bromide, sulfonate and sulfate (with 5, 15, 25, 45 or 60 mols ethylene oxide);
monobehenyl bis(polyethoxy) monoethyl quaternary ammonium chloride, iodide, bromide, sulfonate and sulfate (with 5, 15, 25, 45 or 60 mols ethylene oxide);
monopalmityl bis(polyethoxy) monoethyl quaternary ammonium chloride, iodide, bromide, sulfonate and sulfate (with 5, 15, 25, 45 or 60 mols ethylene oxide);
monosoya bis(polyethoxy) monoethyl quaternary ammonium chloride, iodide, bromide, sulfonate and sulfate (with 5, 15, 25, 45 or 60 mols ethylene oxide);
monooleyl bis(polyethoxy) monoethyl quaternary ammonium chloride, iodide, bromide, sulfonate and sulfate (with 5, 15, 25, 45 or 60 mols ethylene oxide);
monostearyl bis(polyethoxy) monopropyl quaternary ammonium chloride, iodide, bromide, sulfonate and sulfate (with 5, 15, 25, 45 or 60 mols ethylene oxide);
monotallow bis(polyethoxy) monopropyl quaternary ammonium chloride, iodide, bromide, sulfonate and sulfate (with 5, 15, 25, 45 or 60 mols ethylene oxide);
monolauryl bis(polyethoxy) monopropyl quaternary ammonium chloride, iodide, bromide, sulfonate and sulfate (with 5, 15, 25, 45 or 60 mols ethylene oxide);
monococo bis(polyethoxy) monopropyl quaternary ammonium chloride, iodide, bromide, sulfonate and sulfate (with 5, 15, 25, 45 or 60 mols ethylene oxide);
monomyristyl bis(polyethoxy) monopropyl quaternary ammonium chloride, iodide, bromide, sulfonate and sulfate (with 5, 15, 25, 45 or 60 mols ethylene oxide);
monobehenyl bis(polyethoxy) monopropyl quaternary ammonium chloride, iodide, bromide, sulfonate and sulfate (with 5, 15, 25, 45 or 60 mols ethylene oxide);
monopalmityl bis(polyethoxy) monopropyl quaternary ammonium chloride, iodide, bromide, sulfonate and sulfate (with 5, 15, 25, 45 or 60 mols ethylene oxide);
monosoya bis(polyethoxy) monopropyl quaternary ammonium chloride, iodide, bromide, sulfonate and sulfate (with 5, 15, 25, 45 or 60 mols ethylene oxide);

monooleyl bis(polyethoxy) monopropyl quaternary ammonium chloride, iodide, bromide, sulfonate and sulfate (with 5, 15, 25, 45 or 60 mols ethylene oxide);
monostearyl bis(polyethoxy) mono n-butyl quaternary ammonium chloride, iodide, bromide, sulfonate and sulfate (with 5, 15, 25, 45 or 60 mols ethylene oxide);
monotallow bis(polyethoxy) mono n-butyl quaternary ammonium chloride, iodide, bromide, sulfonate and sulfate (with 5, 15, 25, 45 or 60 mols ethylene oxide);
monolauryl bis(polyethoxy) mono n-butyl quaternary ammonium chloride, iodide, bromide, sulfonate and sulfate (with 5, 15, 25, 45 or 60 mols ethylene oxide);
monococo bis(polyethoxy) mono n-butyl quaternary ammonium chloride, iodide, bromide, sulfonate and sulfate (with 5, 15, 25, 45 or 60 mols ethylene oxide);
monomyristyl bis(polyethoxy) mono n-butyl quaternary ammonium chloride, iodide, bromide, sulfonate and sulfate (with 5, 15, 25, 45 or 60 mols ethylene oxide);
monobehenyl bis(polyethoxy) mono n-butyl quaternary ammonium chloride, iodide, bromide, sulfonate and sulfate (with 5, 15, 25, 45 or 60 mols ethylene oxide);
monopalmityl bis(polyethoxy) mono n-butyl quaternary ammonium chloride, iodide, bromide, sulfonate and sulfate (with 5, 15, 25, 45 or 60 mols ethylene oxide);
monosoya bis(polyethoxy) mono n-butyl quaternary ammonium chloride, iodide, bromide, sulfonate and sulfate (with 5, 15, 25, 45 or 60 mols ethylene oxide);
monooleyl bis(polyethoxy) mono n-butyl quaternary ammonium chloride, iodide, bromide, sulfonate and sulfate (with 5, 15, 25, 45 or 60 mols ethylene oxide);
monostearyl bis(polyethoxy) mono secondary butyl quaternary ammonium chloride, iodide, bromide, sulfonate and sulfate (with 5, 15, 25, 45 or 60 mols ethylene oxide);
monotallow bis(polyethoxy) mono secondary butyl quaternary ammonium chloride, iodide, bromide, sulfonate and sulfate (with 5, 15, 25, 45 or 60 mols ethylene oxide);
monolauryl bis(polyethoxy) mono secondary butyl quaternary ammonium chloride, iodide, bromide, sulfonate and sulfate (with 5, 15, 25, 45 or 60 mols ethylene oxide);
monococo bis(polyethoxy) mono secondary butyl quaternary ammonium chloride, iodide, bromide, sulfonate and sulfate (with 5, 15, 25, 45 or 60 mols ethylene oxide);
monomyristyl bis(polyethoxy) secondary butyl quaternary ammonium chloride, iodide, bromide, sulfonate and sulfate (with 5, 15, 25, 45 or 60 mols ethylene oxide);
monobehenyl bis(polyethoxy) mono secondary butyl quaternary ammonium chloride, iodide, bromide, sulfonate and sulfate (with 5, 15, 25, 45 or 60 mols ethylene oxide);
monopalmityl bis(polyethoxy) secondary butyl quaternary ammonium chloride, iodide, bromide, sulfonate and sulfate (with 5, 15, 25, 45 or 60 mols ethylene oxide);
monosoya bis(polyethoxy) mono secondary butyl quaternary ammonium chloride, iodide, bromide, sulfonate and sulfate (with 5, 15, 25, 45, or 60 mols ethylene oxide);
monooleyl bis(polyethoxy) mono secondary butyl quaternary ammonium chloride, iodide, bromide, sulfonate and sulfate (with 5, 15, 25, 45 or 60 mols ethylene oxide);
monostearyl bis(polyethoxy) monoamyl quaternary ammonium chloride, iodide, bromide, sulfonate and sulfate (with 5, 15, 25, 45 or 60 mols ethylene oxide);
monotallow bis(polyethoxy) monoamyl quaternary ammonium chloride, iodide, bromide, sulfonate and sulfate (with 5, 15, 25, 45 or 60 mols ethylene oxide);
monolauryl bis(polyethoxy) monoamyl quaternary ammonium chloride, iodide, bromide, sulfonate and sulfate (with 5, 15, 25, 45 or 60 mols ethylene oxide);
monococo bis(polyethoxy) monoamyl quaternary ammonium chloride, iodide, bromide, sulfonate and sulfate (with 5, 15, 25, 45 or 60 mols ethylene oxide);
monomyristyl bis(polyethoxy) monoamyl quaternary ammonium chloride, iodide, bromide, sulfonate and sulfate (with 5, 15, 25, 45 or 60 mols ethylene oxide);
monobehenyl bis(polyethoxy) monoamyl quaternary ammonium chloride, iodide, bromide, sulfonate and sulfate (with 5, 15, 25, 45 or 60 mols ethylene oxide);
monopalmityl bis(polyethoxy) monoamyl quaternary ammonium chloride, iodide, bromide, sulfonate and sulfate (with 5, 15, 25, 45 or 60 mols ethylene oxide);
monosoya bis(polyethoxy) monoamyl quaternary ammonium chloride, iodide, bromide, sulfonate and sulfate (with 5, 15, 25, 45 or 60 mols ethylene oxide);
monooleyl bis(polyethoxy) monoamyl quaternary ammonium chloride, iodide, bromide, sulfonate and sulfate (with 5, 15, 25, 45 or 60 mols ethylene oxide);
monostearyl bis(polyethoxy) monohexyl quaternary ammonium chloride, iodide, bromide, sulfonate and sulfate (with 5, 15, 25, 45 or 60 mols ethylene oxide);
monotallow bis(polyethoxy) monohexyl quaternary ammonium chloride, iodide, bromide, sulfonate and sulfate (with 5, 15, 25, 45 or 60 mols ethylene oxide);
monolauryl bis(polyethoxy) monohexyl quaternary ammonium chloride, iodide, bromide, sulfonate and sulfate (with 5, 15, 25, 45 or 60 mols ethylene oxide);
monococo bis(polyethoxy) monohexyl quaternary ammonium chloride, iodide, bromide, sulfonate and sulfate (with 5, 15, 25, 45 or 60 mols ethylene oxide);
monomyristyl bis(polyethoxy) monohexyl quaternary ammonium chloride, iodide, bromide, sulfonate and sulfate (with 5, 15, 25, 45 or 60 mols ethylene oxide);
monobehenyl bis(polyethoxy) monohexyl quaternary ammonium chloride, iodide, bromide, sulfonate and sulfate (with 5, 15, 25, 45 or 60 mols ethylene oxide);
monopalmityl bis(polyethoxy) monohexyl quaternary ammonium chloride, iodide, bromide, sulfonate and sulfate (with 5, 15, 25, 45 or 60 mols ethylene oxide);
monosoya bis(polyethoxy) monohexyl quaternary ammonium chloride, iodide, bromide, sulfonate and sulfate (with 5, 15, 25, 45 or 60 mols ethylene oxide);
monooleyl bis(polyethoxy) monohexyl quaternary ammonium chloride, iodide, bromide, sulfonate and sulfate (with 5, 15, 25, 45 or 60 mols ethyelne oxide);
monostearyl bis(polyethoxy) monobenzyl quaternary ammonium chloride, iodide, bromide, sulfonate and sulfate (with 5, 15, 25, 45 or 60 mols ethylene oxide);
monotallow bis(polyethoxy) monobenzyl quaternary ammonium chloride, iodide, bromide, sulfonate and sulfate (with 5, 15, 25, 45 or 60 mols ethylene oxide);
monolauryl bis(polyethoxy) monobenzyl quaternary ammonium chloride, iodide, bromide, sulfonate and sulfate (with 5, 15, 25, 45 or 60 mols ethylene oxide);
monococo bis(polyethoxy) monobenzyl quaternary ammonium chloride, iodide, bromide, sulfonate and sulfate (with 5, 15, 25, 45 or 60 mols ethylene oxide);

monomyristyl bis(polyethoxy) monobenzyl quaternary ammonium chloride, iodide, bromide, sulfonate and sulfate (with 5, 15, 25, 45 or 60 mols ethylene oxide);

monobehenyl bis(polyethoxy) monobenzyl quaternary ammonium chloride, iodide, bromide, sulfonate and sulfate (with 5, 15, 25, 45 or 60 mols ethylene oxide);

monopalmityl bis(polyethoxy) monobenzyl quaternary ammonium chloride, iodide, bromide, sulfonate and sulfate (with 5, 15, 25, 45 or 60 mols ethylene oxide);

monosoya bis(polyethoxy) monobenzyl quaternary ammonium chloride, iodide, bromide, sulfonate and sulfate (with 5, 15, 25, 45 or 60 molss ethylene oxide);

monooleyl bis(polyethoxy) monobenzyl quaternary ammonium chloride, iodide, bromide, sulfonate and sulfate (with 5, 15, 25, 45 or 60 mols ethylene oxide);

monostearyl bis(polypropoxy) monomethyl quaternary ammonium chloride, iodide, bromide, sulfonate and sulfate (with 5, 15, 25, 45 or 60 mols propylene oxide);

monotallow bis(polypropoxy) monomethyl quaternary ammonium chloride, iodide, bromide, sulfonate and sulfate (with 5, 15, 25, 45 or 60 mols propylene oxide);

monolauryl bis(polypropoxy) monomethyl quaternary ammonium chloride, iodide, bromide, sulfonate and sulfate (with 5, 15, 25, 45 or 60 mols propylene oxide);

monococo bis(polypropoxy) monomethyl quaternary ammonium chloride, iodide, bromide, sulfonate and sulfate (with 5, 15, 25, 45 or 60 mols propylene oxide);

monomyristyl bis(polypropoxy) monomethyl quaternary ammonium chloride, iodide, bromide, sulfonate and sulfate (with 5, 15, 25, 45 or 60 mols propylene oxide);

monobehenyl bis(polypropoxy) monomethyl quaternary ammonium chloride, iodide, bromide, sulfonate and sulfate (with 5, 15, 25, 45 or 60 mols propylene oxide);

monopalmityl bis(polypropoxy) monomethyl quaternary ammonium chloride, iodide, bromide, sulfonate and sulfate (with 5, 15, 25, 45 or 60 mols propylene oxide);

monosoya bis(polypropoxy) monomethyl quaternary ammonium chloride, iodide, bromide, sulfonate and sulfate (with 5, 15, 25, 45 or 60 mols propylene oxide);

monooleyl bis(polypropoxy) monomethyl quaternary ammonium chloride, iodide, bromide, sulfonate and sulfate (with 5, 15, 25, 45 or 60 mols propylene oxide);

monostearyl bis(polypropoxy) monoethyl quaternary ammonium chloride, iodide, bromide, sulfonate and sulfate (with 5, 15, 25, 45 or 60 mols propylene oxide);

monotallow bis(polypropoxy) monoethyl quaternary ammonium chloride, iodide, bromide, sulfonate and sulfate (with 5, 15, 25, 45 or 60 mols propylene oxide);

monolauryl bis(polypropoxy) monoethyl quaternary ammonium chloride, iodide, bromide, sulfonate and sulfate (with 5, 15, 25, 45 or 60 mols propylene oxide);

monococo bis(polypropoxy) monoethyl quaternary ammonium chloride, iodide, bromide, sulfonate and sulfate (with 5, 15, 25, 45 or 60 mols propylene oxide);

monomyristyl bis(polypropoxy) monoethyl quaternary ammonium chloride, iodide, bromide, sulfonate and sulfate (with 5, 15, 25, 45 or 60 mols propylene oxide);

monobehenyl bis(polypropoxy) monoethyl quaternary ammonium chloride, iodide, bromide, sulfonate and sulfate (with 5, 15, 25, 45 or 60 mols propylene oxide);

monopalmityl bis(polypropoxy) monoethyl quaternary ammonium chloride, iodide, bromide, sulfonate and sulfate (with 5, 15, 25, 45 or 60 mols propylene oxide);

monosoya bis(polypropoxy) monoethyl quaternary ammonium chloride, iodide, bromide, sulfonate and sulfate (with 5, 15, 25, 45 or 60 mols propylene oxide);

monooleyl bis(polypropoxy) monoethyl quaternary ammonium chloride, iodide, bromide, sulfonate and sulfate (with 5, 15, 25, 45 or 60 mols propylene oxide);

monostearyl bis(polypropoxy) monopropyl quaternary ammonium chloride, iodide, bromide, sulfonate and sulfate (with 5, 15, 25, 45 or 60 mols propylene oxide);

monotallow bis(polypropoxy) monopropyl quaternary ammonium chloride, iodide, bromide, sulfonate and sulfate (with 5, 15, 25, 45 or 60 mols propylene oxide);

monolauryl bis(polypropoxy) monopropyl quaternary ammonium chloride, iodide, bromide, sulfonate and sulfate (with 5, 15, 25, 45 or 60 mols propylene oxide);

monococo bis(polypropoxy) monopropyl quaternary ammonium chloride, iodide, bromide, sulfonate and sulfate (with 5, 15, 25, 45 or 60 mols propylene oxide);

monomyristyl bis(polypropoxy) monopropyl quaternary ammonium chloride, iodide, bromide, sulfonate and sulfate (with 5, 15, 25, 45 or 60 mols propylene oxide);

monobehenyl bis(polypropoxy) monopropyl quaternary ammonium chloride, iodide, bromide, sulfonate and sulfate (with 5, 15, 25, 45 or 60 mols propylene oxide);

monopalmityl bis(polypropoxy) monopropyl quaternary ammonium chloride, iodide, bromide, sulfonate and sulfate (with 5, 15, 25, 45 or 60 mols propylene oxide);

monosoya bis(polypropoxy) monopropyl quaternary ammonium chloride, iodide, bromide, sulfonate and sulfate (with 5, 15, 25, 45 or 60 mols propylene oxide);

monooleyl bis(polypropoxy) monopropyl quaternary ammonium chloride, iodide, bromide, sulfonate and sulfate (with 5, 15, 25, 45 or 60 mols propylene oxide);

monostearyl bis(polypropoxy) mono n-butyl quaternary ammonium chloride, iodide, bromide, sulfonate and sulfate (with 5, 15, 25, 45 or 60 mols propylene oxide);

monotallow bis(polypropoxy) mono n-butyl quaternary ammonium chloride, iodide, bromide, sulfonate and sulfate (with 5, 15, 25, 45 or 60 mols propylene oxide);

monolauryl bis(polypropoxy) mono n-butyl quaternary ammonium chloride, iodide, bromide, sulfonate and sulfate (with 5, 15, 25, 45 or 60 mols propylene oxide);

monococo bis(polypropoxy) mono n-butyl quaternary ammonium chloride, iodide, bromide, sulfonate and sulfate (with 5, 15, 25, 45 or 60 mols propylene oxide);

monomyristyl bis(polypropoxy) mono n-butyl quaternary ammonium chloride, iodide, bromide, sulfonate and sulfate (with 5, 15, 25, 45 or 60 mols propylene oxide);

monobehenyl bis(polypropoxy) mono n-butyl quaternary ammonium chloride, iodide, bromide, sulfonate and sulfate (with 5, 15, 25, 45 or 60 mols propylene oxide);

monopalmityl bis(polypropoxy) mono n-butyl quaternary ammonium chloride, iodide, bromide, sulfonate and sulfate (with 5, 15, 25, 45 or 60 mols propylene oxide);

monosoya bis(polypropoxy) mono n-butyl quaternary ammonium chloride, iodide, bromide, sulfonate and sulfate (with 5, 15, 25, 45 or 60 mols propylene oxide);

monooleyl bis(polypropoxy) mono n-butyl quaternary ammonium chloride, iodide, bromide, sulfonate and sulfate (with 5, 15, 25, 45 or 60 mols propylene oxide);

monostearyl bis(polypropoxy) mono secondary butyl quaternary ammonium chloride, iodide, bromide, sulfonate and sulfate (with 5, 15, 25, 45 or 60 mols propylene oxide);

monotallow bis(polypropoxy) mono secondary butyl quaternary ammonium chloride, iodide, bromide, sulfonate and sulfate (with 5, 15, 25, 45 or 60 mols propylene oxide);

monolauryl bis(polypropoxy) mono secondary butyl quaternary ammonium chloride, iodide, bromide, sulfonate and sulfate (with 5, 15, 25, 45 or 60 mols propylene oxide);

monococo bis(polypropoxy) mono secondary butyl quaternary ammonium chloride, iodide, bromide, sulfonate and sulfate (with 5, 15, 25, 45 or 60 mols propylene oxide);

monomyristyl bis(polypropoxy) mono secondary butyl quaternary ammonium chloride, iodide, bromide, sulfonate and sulfate (with 5, 15, 25, 45 or 60 mols propylene oxide);

monobehenyl bis(polypropoxy) mono secondary butyl quaternary ammonium chloride, iodide, bromide, sulfonate and sulfate (with 5, 15, 25, 45 or 60 mols propylene oxide);

monopalmityl bis(polypropoxy) mono secondary butyl quaternary ammonium chloride, iodide, bromide, sulfonate and sulfate (with 5, 15, 25, 45 or 60 mols propylene oxide);

monosoya bis(polypropoxy) mono secondary butyl quaternary ammonium chloride, iodide, bromide, sulfonate and sulfate (with 5, 15, 25, 45 or 60 mols propylene oxide);

monooleyl bis(polypropoxy) mono secondary butyl quaternary ammonium chloride, iodide, bromide, sulfonate and sulfate (with 5, 15, 25, 45 or 60 mols propylene oxide);

monostearyl bis(polypropoxy) monoamyl quaternary ammonium chloride, iodide, bromide, sulfonate and sulfate (with 5, 15, 25, 45 or 60 mols propylene oxide);

monotallow bis(polypropoxy) monoamyl quaternary ammonium chloride, iodide, bromide, sulfonate and sulfate (with 5, 15, 25, 45 or 60 mols propylene oxide);

monolauryl bis(polypropoxy)monoamyl quaternary ammonium chloride, iodide, bromide, sulfonate and sulfate (with 5, 15, 25, 45 or 60 mols propylene oxide);

monococo bis(polypropoxy) monoamyl quaternary ammonium chloride, iodide, bromide, sulfonate and sulfate (with 5, 15, 25, 45 or 60 mols propylene oxide);

monomyristyl bis(polypropoxy) monoamyl quaternary ammonium chloride, iodide, bromide, sulfonate and sulfate (with 5, 15, 25, 45 or 60 mols propylene oxide);

monobehenyl bis(polypropoxy) monoamyl quaternary ammonium chloride, iodide, bromide, sulfonate and sulfate (with 5, 25, 45 or 60 mols propylene oxide);

monopalmityl bis(polypropoxy) monoamyl quaternary ammonium chloride, iodide, bromide, sulfonate and sulfate (with 5, 15, 25, 45 or 60 mols propylene oxide);

monosoya bis(polypropoxy) monoamyl quaternary ammonium chloride, iodide, bromide, sulfonate and sulfate (with 5, 15, 25, 45 or 60 mols propylene oxide);

monooleyl bis(polypropoxy) monoamyl quaternary ammonium chloride, iodide, bromide, sulfonate and sulfate (with 5, 15, 25, 45 or 60 mols propylene oxide);

monostearyl bis(polypropoxy) monohexyl quaternary ammonium chloride, iodide, bromide, sulfonate and sulfate (with 5, 15, 25, 45 or 60 mols propylene oxide);

monotallow bis(polypropoxy) monohexyl quaternary ammonium chloride, iodide, bromide, sulfonate and sulfate (with 5, 15, 25, 45 or 60 mols propylene oxide);

monolauryl bis(polypropoxy)monohexyl quaternary ammonium chloride, iodide, bromide, sulfonate and sulfate (with 5, 15, 25, 45 or 60 mols propylene oxide);

monococo bis(polypropoxy) monohexyl quaternary ammonium chloride, iodide, bromide, sulfonate and sulfate (with 5, 15, 25, 45 or 60 mols propylene oxide);

monomyristyl bis(polypropoxy) monohexyl quaternary ammonium chloride, iodide, bromide, sulfonate and sulfate (with 5, 15, 25, 45 or 60 mols propylene oxide);

monobehenyl bis(polypropoxy) monohexyl quaternary ammonium chloride, iodide, bromide, sulfonate and sulfate (with 5, 15, 25, 45 or 60 mols propylene oxide);

monopalmityl bis(polypropoxy) monohexyl quaternary ammonium chloride, iodide, bromide, sulfonate and sulfate (with 5, 15, 25, 45 or 60 mols propylene oxide);

monosoya bis(polypropoxy) monohexyl quaternary ammonium chloride, iodide, bromide, sulfonate and sulfate (with 5, 15, 25, 45 or 60 mols propylene oxide);

monooleyl bis(polypropoxy) monohexyl quaternary ammonium chloride, iodide, bromide, sulfonate and sulfate (with 5, 15, 25, 45 or 60 mols propylene oxide);

monostearyl bis(polypropoxy) monobenzyl quaternary ammonium chloride, iodide, bromide, sulfonate and sulfate (with 5, 15, 25, 45 or 60 mols propylene oxide);

monotallow bis(polypropoxy) monobenzyl quaternary ammonium chloride, iodide, bromide, sulfonate and sulfate (with 5, 15, 25, 45, or 60 mols propylene oxide);

monolauryl bis(polypropoxy) monobenzyl quaternary ammonium chloride, iodide, bromide, sulfonate and sulfate (with 5, 15, 25, 45 or 60 mols propylene oxide);

monococo bis(polypropoxy) monobenzyl quaternary ammonium chloride, iodide, bromide, sulfonate and sulfate (with 5, 15, 25, 45 or 60 mols propylene oxide);

monomyristyl bis(polypropoxy) monobenzyl quaternary ammonium chloride, iodide, bromide, sulfonate and sulfate (with 5, 15, 25, 45 or 60 mols propylene oxide);

monobehenyl bis(polypropoxy) monobenzyl quaternary ammonium chloride, iodide, bromide, sulfonate and sulfate (with 5, 15, 25, 45 or 60 mols propylene oxide);

monopalmityl bis(polypropoxy) monobenzyl quaternary ammonium chloride, iodide, bromide, sulfonate and sulfate (with 5, 15, 25, 45 or 60 mols propylene oxide);

monosoya bis(polypropoxy) monobenzyl quaternary ammonium chloride, iodide, bromide, sulfonate and sulfate (with 5, 15, 25, 45 or 60 mols propylene oxide);

monooleyl bis(polypropoxy) monobenzyl quaternary ammonium chloride, iodide, bromide, sulfonate and sulfate (with 5, 15, 25, 45 or 60 mols propylene oxide);

distearyl mono (polypropoxy) monomethyl quaternary ammonium chloride, iodide, bromide, sulfonate and sulfate (with 5, 15, 25, 45 or 60 mols propylene oxide);

ditallow mono (polypropoxy) monomethyl quaternary ammonium chloride, iodide, bromide, sulfonate and sulfate (with 5, 15, 25, 45 or 60 mols propylene oxide);

dilauryl mono (polypropoxy) monomethyl quaternary ammonium chloride, iodide, bromide, sulfonate and sulfate (with 5, 15, 25, 45 or 60 mols propylene oxide);

dicoco mono (polypropoxy) monomethyl quaternary ammonium chloride, iodide, bromide, sulfonate and sulfate (with 5, 15, 25, 45 or 60 mols propylene oxide);

distearyl mono(polypropoxy) monoethyl quaternary ammonium chloride, iodide, bromide, sulfonate and sulfate (with 5, 15, 25, 45 or 60 mols propylene oxide);

ditallow mono(polypropoxy) monoethyl quaternary ammonium chloride, iodide, bromide, sulfonate and sulfate (with 5, 15, 25, 45 or 60 mols propylene oxide);

dilauryl mono(polypropoxy) monoethyl quaternary ammonium chloride, iodide, bromide, sulfonate and sulfate (with 5, 15, 25, 45 or 60 mols propylene oxide);

dicoco mono(polypropoxy) monoethyl quaternary ammonium chloride, iodide, bromide, sulfonate and sulfate (with 5, 15, 25, 45 or 60 mols propylene oxide);

distearyl mono(polypropoxy) monopropyl quaternary ammonium chloride, iodide, bromide, sulfonate and sulfate (with 5, 15, 25, 45 or 60 mols propylene oxide);

ditallow mono(polypropoxy) monopropyl quaternary ammonium chloride, iodide, bromide, sulfonate and sulfate (with 5, 15, 25, 45 or 60 mols propylene oxide);

dilauryl mono(polypropoxy) monopropyl quaternary ammonium chloride, iodide, bromide, sulfonate and sulfate (with 5, 15, 25, 45 or 60 mols propylene oxide);

dicoco mono(polypropoxy) monopropyl quaternary ammonium chloride, iodide, bromide, sulfonate and sulfate (with 5, 15, 25, 45 or 60 mols propylene oxide);

distearyl mono(polypropoxy) mono n-butyl quaternary ammonium chloride, iodide, bromide, sulfonate and sulfate (with 5, 15, 25, 45 or 60 mols propylene oxide);

ditallow mono(polypropoxy) mono n-butyl quaternary ammonium chloride, iodide, bromide, sulfonate and sulfate (with 5, 15, 25, 45 or 60 mols propylene oxide);

dilauryl mono(polypropoxy) mono n-butyl quaternary ammonium chloride, iodide, bromide, sulfonate and sulfate (with 5, 15, 25, 45 or 60 mols propylene oxide);

dicoco mono(polypropoxy) mono n-butyl quaternary ammonium chloride, iodide, bromide sulfonate and sulfate (with 5, 15, 25, 45 or 60 mols propylene oxide);

distearyl mono(polypropoxy) mono secondary butyl quaternary ammonium chloride, iodide, bromide, sulfonate and sulfate (with 5, 15, 25, 45 or 60 mols propylene oxide);

ditallow mono(polypropoxy) mono secondary butyl quaternary ammonium chloride, iodide, bromide, sulfonate and sulfate (with 5, 15, 25, 45 or 60 mols propylene oxide);

dilauryl mono(polypropoxy) mono secondary butyl quaternary ammonium chloride, iodide, bromide, sulfonate and sulfate (with 5, 15, 25, 45 or 60 mols propylene oxide);

dicoco mono(polypropoxy) mono secondary butyl quaternary ammonium chloride, iodide, bromide, sulfonate and sulfate (with 5, 15, 25, 45 or 60 mols propylene oxide);

distearyl mono(polypropoxy) monoamyl quaternary ammonium chloride, iodide, bromide, sulfonate and sulfate (with 5, 15, 25, 45 or 60 mols propylene oxide);

ditallow mono(polypropoxy) monoamyl quaternary ammonium chloride, iodide, bromide, sulfonate and sulfate (with 5, 15, 25, 45 or 60 mols propylene oxide);

dilauryl mono(polypropoxy) monoamyl quaternary ammonium chloride, iodide, bromide, sulfonate and sulfate (with 5, 15, 25, 45 or 60 mols propylene oxide);

dicoco mono(polypropoxy) monoamyl quaternary ammonium chloride, iodide, bromide, sulfonate and sulfate (with 5, 15, 25, 45 or 60 mols propylene oxide);

distearyl mono(polypropoxy) monohexyl quaternary ammonium chloride, iodide, bromide, sulfonate and sulfate (with 5, 15, 25, 45 or 60 mols propylene oxide);

ditallow mono(polypropoxy) monohexyl quaternary ammonium chloride, iodide, bromide, sulfonate and sulfate (with 5, 15, 25, 45 or 60 mols propylene oxide);

dilauryl mono(polypropoxy) monohexyl quaternary ammonium chloride, iodide, bromide, sulfonate and sulfate (with 5, 15, 25, 45 or 60 mols propylene oxide);

dicoco mono(polypropoxy) monohexyl quaternary ammonium chloride, iodide, bromide, sulfonate and sulfate (with 5, 15, 25 45 or 60 mols propylene oxide);

distearyl mono(polypropoxy) monobenzyl quaternary ammonium chloride, iodide, bromide, sulfonate and sulfate (with 5, 15, 25, 45 or 60 mols propylene oxide);

ditallow mono(polypropoxy) monobenzyl quaternary ammonium chloride, iodide, bromide, sulfonate and sulfate (with 5, 15, 25, 45 or 60 mols propylene oxide);

dilauryl mono(polypropoxy) monobenzyl quaternary ammonium chloride, iodide, bromide, sulfonate and sulfate (with 5, 15, 25, 45 or 60 mols propylene oxide);

dicoco mono(polypropoxy) monobenzyl quaternary ammonium chloride, iodide, bromide, sulfonate and sulfate (with 5, 15, 25, 45 or 60 mols propylene oxide);

distearyl mono(polyethoxy) monomethyl quaternary ammonium chloride, iodide, bromide, sulfonate and sulfate (with 5, 15, 25, 45 or 60 mols ethylene oxide);

ditallow mono(polyethoxy) monomethyl quaternary ammonium chloride, iodide, bromide, sulfonate and sulfate (with 5, 15, 25, 45 or 60 mols ethylene oxide);

dilauryl mono(polyethoxy) monomethyl quaternary ammonium chloride, iodide, bromide, sulfonate and sulfate (with 5, 15, 25, 45 or 60 mols ethylene oxide);

dicoco mono(polyethoxy) monomethyl quaternary ammonium chloride, iodide, bromide, sulfonate and sulfate (with 5, 15, 25, 45 or 60 mols ethylene oxide);

distearyl mono(polyethoxy) monoethyl quaternary ammonium chloride, iodide, bromide, sulfonate and sulfate (with 5, 15, 25, 45 or 60 mols ethylene oxide);

ditallow mono(polyethoxy) monoethyl quaternary ammonium chloride, iodide, bromide, sulfonate and sulfate (with 5, 15, 25, 45 or 60 mols ethylene oxide);

dilauryl mono(polyethoxy) monoethyl quaternary ammonium chloride, iodide, bromide, sulfonate and sulfate (with 5, 15, 25, 45 or 60 mols ethylene oxide);

dicoco mono(polyethoxy) monoethyl quaternary ammonium chloride, iodide, bromide, sulfonate and sulfate (with 5, 15, 25, 45 or 60 mols ethylene oxide);

distearyl mono(polyethoxy) monopropyl quaternary ammonium chloride, iodide, bromide, sulfonate and sulfate (with 5, 15, 25, 45 or 60 mols ethylene oxide);

ditallow mono(polyethoxy) monopropyl quaternarym ammonium chloride, iodide, bromide, sulfonate and sulfate (with 5, 15, 25, 45 or 60 mols ethylene oxide);

dilauryl mono(polyethoxy) monopropyl quaternary ammonium chloride, iodide, bromide, sulfonate and sulfate (with 5, 15, 25, 45 or 60 mols ethylene oxide);

dicoco mono(polyethoxy) monopropyl quaternary ammonium chloride, iodide, bromide, sulfonate and sulfate (with 5, 15, 25, 45 or 60 mols ethylene oxide);

distearyl mono(polyethoxy) mono n-butyl quaternary ammonium chloride, iodide, bromide, sulfonate and sulfate (with 5, 15, 25, 45 or 60 mols ethylene oxide);

ditallow mono(polyethoxy) mono n-butyl quaternary ammonium chloride, iodide, bromide, bulfonate and sulfate (with 5, 15, 25, 45 or 60 mols ethylene oxide);

dilauryl mono(polyethoxy) mono n-butyl quaternary ammonium chloride, iodide, bromide, sulfonate and sulfate (with 5, 15, 25, 45 or 60 mols ethylene oxide);

dicoco mono(polyethoxy) mono n-butyl quaternary ammonium chloride, iodide, bromide, sulfonate and sulfate (with 5, 15, 25, 45 or 60 mols ethylene oxide);

distearyl mono(polyethoxy) mono secondary butyl quaternary ammonium chloride, iodide, bromide, sulfonate and sulfate (with 5, 15, 25, 45 or 60 mols ethylene oxide);

ditallow mono(polyethoxy) mono secondary butyl quaternary ammonium chloride, iodide, bromide, sulfonate and sulfate (with 5, 15, 25, 45 or 60 mols ethylene oxide);

dilauryl mono(polyethoxy) mono secondary butyl quaternary ammonium chloride, iodide, bromide, sulfonate and sulfate (with 5, 15, 25, 45 or 60 mols ethylene oxide);

dicoco mono(polyethoxy) mono secondary butyl quaternary ammonium chloride, iodide, bromide, sulfonate and sulfate (with 5, 15, 25, 45 or 60 mols ethylene oxide);

distearyl mono(polyethoxy) monoamyl quaternary ammonium chloride, iodide, bromide, sulfonate and sulfate (with 5, 15, 25, 45 or 60 mols ethylene oxide);

ditallow mono(polyethoxy) monoamyl quaternary ammonium chloride, iodide, bromide, sulfonate and sulfate (with 5, 15, 25, 45 or 60 mols ethylene oxide);

dilauryl mono(polyethoxy) monoamyl quaternary ammonium chloride, iodide, bromide, sulfonate and sulfate (with 5, 15, 25, 45 or 60 mols ethylene oxide);

dicoco mono(polyethoxy) monoamyl quaternary ammonium chloride, iodide, bromide, sulfonate and sulfate (with 5, 15, 25, 45 or 60 mols ethylene oxide);

distearyl mono(polyethoxy) monohexyl quaternary ammonium chloride, iodide, bromide, sulfonate and sulfate (with 5, 15, 25, 45 or 60 mols ethylene oxide);

ditallow mono(polyethoxy) monohexyl quaternary ammonium chloride, iodide, bromide, sulfonate and sulfate (with 5, 15, 25, 45 or 60 mols ethylene oxide);

dilauryl mono(polyethoxy) monohexyl quaternary ammonium chloride, iodide, bromide, sulfonate and sulfate (with 5, 15, 25, 45 or 60 mols ethylene oxide);

dicoco mono(polyethoxy) monohexyl quaternary ammonium chloride, iodide, bromide, sulfonate and sulfate (with 5, 15, 25, 45 or 60 mols ethylene oxide);

distearyl mono(polyethoxy) monobenzyl quaternary ammonium chloride, iodide, bromide, sulfonate and sulfate (with 5, 15, 25, 45 or 60 mols ethylene oxide);

ditallow mono(polyethoxy) monobenzyl quaternary ammonium chloride, iodide, bromide, sulfonate and sulfate (with 5, 15, 25, 45 or 60 mols ethylene oxide);

dilauryl mono(polyethoxy) monobenzyl quaternary ammonium chloride, iodide, bromide, sulfonate and sulfate (with 5, 15, 25, 45 or 60 mols ethylene oxide);

dicoco mono(polyethoxy) monobenzyl quaternary ammonium chloride, iodide, bromide, sulfonate and sulfate (with 5, 15, 25, 45 or 60 mols ethylene oxide);

monostearyl mono(polyethoxy) methyl methyl quaternary ammonium chloride, iodide, bromide, sulfonate and sulfate (with 5, 15, 25, 45 or 60 mols ethylene oxide);

monotallow mono(polyethoxy) methyl methyl quaternary ammonium chloride, iodide, bromide, sulfonate and sulfate (with 5, 15, 25, 45 or 60 mols ethylene oxide);

monolauryl mono(polyethoxy) methyl methyl quaternary ammonium chloride, iodide, bromide, sulfonate and sulfate (with 5, 15, 25, 45 or 60 mols ethylene oxide);

monococo mono(polyethoxy) methyl methyl quaternary ammonium chloride, iodide, bromide, sulfonate and sulfate (with 5, 15, 25, 45 or 60 mols ethylene oxide);

monomyristyl mono(polyethoxy) methyl methyl quaternary ammonium chloride, iodide, bromide, sulfonate and sulfate (with 5, 15, 25, 45 or 60 mols ethylene oxide);

monobehenyl mono(polyethoxy) methyl methyl quaternary ammonium chloride, iodide, bromide, sulfonate and sulfate (with 5, 15, 25, 45 or 60 mols ethylene oxide);

monopalmityl mono(polyethoxy) methyl methyl quaternary ammonium chloride, iodide, bromide, sulfonate and sulfate (with 5, 15, 25, 45, or 60 mols ethylene oxide);

monosoya mono(polyethoxy) methyl methyl quaternary ammonium chloride, iodide, bromide, sulfonate and sulfate (with 5, 15, 25, 45 or 60 mols ethylene oxide);

monooleyl mono(polyethoxy) methyl methyl quaternary ammonium chloride, iodide, bromide, sulfonate and sulfate (with 5, 15, 25, 45 or 60 mols ethylene oxide);

monostearyl mono(polyethoxy) ethyl methyl quaternary ammonium chloride, iodide, bromide, sulfonate and sulfate (with 5, 15, 25, 45 or 60 mols ethylene oxide);

monotallow mono(polyethoxy) ethyl methyl quaternary ammonium chloride, iodide, bromide, sulfonate and sulfate (with 5, 15, 25, 45 or 60 mols ethylene oxide);

monolauryl mono(polyethoxy) ethyl methyl quaternary ammonium chloride, iodide, bromide, sulfonate and sulfate (with 5, 15, 25, 45 or 60 mols ethylene oxide);

monococo mono(polyethoxy) ethyl methyl quaternary ammonium chloride, iodide, bromide, sulfonate and sulfate (with 5, 15, 25, 45 or 60 mols ethylene oxide);

monomyristyl mono(polyethoxy) ethyl methyl quaternary ammonium chloride, iodide, bromide, sulfonate and sulfate (with 5, 15, 25, 45 or 60 mols ethylene oxide);

monobehenyl mono(polyethoxy) ethyl methyl quaternary ammonium chloride, iodide, bromide, sulfonate and sulfate (with 5, 15, 25, 45 or 60 mols ethylene oxide);

monopalmityl mono(polyethoxy) ethyl methyl quaternary ammonium chloride, iodide, bromide, sulfonate and sulfate (with 5, 15, 25, 45 or 60 mols ethylene oxide);

monosoya mono(polyethoxy) ethyl methyl quaternary ammonium chloride, iodide, bromide, sulfonate and sulfate (with 5, 15, 25, 45 or 60 mols ethylene oxide);

monooleyl mono(polyethoxy) ethyl methyl quaternary ammonium chloride, iodide, bromide, sulfonate and sulfate (with 5, 15, 25, 45 or 60 mols ethylene oxide);

monostearyl mono(polyethoxy) propyl methyl quaternary ammonium chloride, iodide, bromide, sulfonate and sulfate (with 5, 15, 25, 45 or 60 mols ethylene oxide);

monotallow mono(polyethoxy) propyl methyl quaternary ammonium chloride, iodide, bromide, sulfonate and sulfate (with 5, 15, 25, 45 or 60 mols ethylene oxide);

monolauryl mono(polyethoxy) propyl methyl quaternary ammonium chloride, iodide, bromide, sulfonate and sulfate (with 5, 15, 25, 45 or 60 mols ethylene oxide);

monococo mono(polyethoxy) propyl methyl quaternary ammonium chloride, iodide, bromide, sulfonate and sulfate (with 5, 15, 25, 45 or 60 mols ethylene oxide);

monomyristyl mono(polyethoxy) propyl methyl quaternary ammonium chloride, iodide, bromide, sulfonate and sulfate (with 5, 15, 25, 45 or 60 mols ethylene oxide); monobehenyl mono(polyethoxy) propyl methyl quaternary ammonium chloride, iodide, bromide, sulfonate and sulfate (with 5, 15, 25, 45 or 60 mols ethylene oxide);

monopalmityl mono(polyethoxy) propyl methyl quaternary ammonium chloride, iodide, bromide, sulfonate and sulfate (with 5, 15, 25, 45 or 60 mols ethylene oxide);

monosoya mono(polyethoxy) propyl methyl quaternary ammonium chloride, iodide, bromide, sulfonate and sulfate (with 5, 15, 25, 45 or 60 mols ethylene oxide);

monooleyl mono(polyethoxy) propyl methyl quaternary ammonium chloride, iodide, bromide, sulfonate and sulfate (with 5, 15, 25, 45 or 60 mols ethylene oxide);

monostearyl mono(polyethoxy) n-butyl methyl quaternary ammonium chloride, iodide, bromide, sulfonate and sulfate (with 5, 15, 25, 45 or 60 mols ethylene oxide);

monotallow mono(polyethoxy) n-butyl methyl quaternary ammonium chloride, iodide, bromide, sulfonate and sulfate (with 5, 15, 25, 45 or 60 mols ethylene oxide);

monolauryl mono(polyethoxy) n-butyl methyl quaternary ammonium chloride, iodide, bromide, sulfonate and sulfate (with 5, 15, 25, 45 or 60 mols ethylene oxide);

monococo mono(polyethoxy) n-butyl methyl quaternary ammonium cloride, iodide, bromide, sulfonate and sulfate (with 5, 15, 25, 45 or 60 mols ethylene oxide);

monomyristyl mono(polyethoxy) n-butyl methyl quaternary ammonium chloride, iodide, bromide, sulfonate and sulfate (with 5, 15, 25, 45 or 60 mols ethylene oxide);

monobehenyl mono(polyethoxy) n-butyl methyl quaternary ammonium chloride, iodide, bromide, sulfonate and sulfate (with 5, 15, 25, 45 or 60 mols ethylene oxide);

monopalmityl mono(polyethoxy) n-butyl methyl quaternary ammonium chloride, iodide, bromide, sulfonate and sulfate (with 5, 15, 25, 45 or 60 mols ethylene oxide);

monosoya mono(polyethoxy) n-butyl methyl quaternary ammonium chloride, iodide, bromide, sulfonate and sulfate (with 5, 15, 25, 45 or 60 mols ethylene oxide);

monooleyl mono(polyethoxy) n-butyl methyl quaternary ammonium chloride, iodide, bromide, sulfonate and sulfate (with 5, 15, 25, 45 or 60 mols ethylene oxide);

monostearyl mono(polyethoxy) secondary butyl methyl quaternary ammonium chloride, iodide, bromide, sulfonate and sulfate (with 5, 15, 25, 45 or 60 mols ethylene oxide);

monotallow mono(polyethoxy) secondary butyl methyl quaternary ammonium chloride, iodide, bromide, sulfonate and sulfate (with 5, 15, 25, 45 or 60 mols ethylene oxide);

monolauryl mono(polyethoxy) secondary butyl methyl quaternary ammonium chloride, iodide, bromide, sulfonate and sulfate (with 5, 15, 25, 45 or 60 mols ethylene oxide);

monococo mono(polyethoxy) secondary butyl methyl quaternary ammonium chloride, iodide, bromide, sulfonate and sulfate (with 5, 15, 25, 45 or 60 mols ethylene oxide);

monomyristyl mono(polyethoxy) secondary butyl methyl quaternary ammonium chloride, iodide, bromide, sulfonate and sulfate (with 5, 15, 25, 45 or 60 mols ethylene oxide);

monobehenyl mono(polyethoxy) secondary butyl methyl quaternary ammonium chloride, iodide, bromide, sulfonate and sulfate (with 5, 15, 25, 45 or 60 mols ethylene oxide);

monopalmityl mono(polyethoxy) secondary butyl methyl quaternary ammonium chloride, iodide, bromide, sulfonate and sulfate (with 5, 15, 25, 45 or 60 mols ethylene oxide);

monosoya mono(polyethoxy) secondary butyl methyl quaternary ammonium chloride, iodide, bromide, sulfonate and sulfate (with 5, 15, 25, 45 or 60 mols ethylene oxide);

monooleyl mono(polyethoxy) secondary butyl methyl quaternary ammonium chloride, iodide, bromide, sulfonate and sulfate (with 5, 15, 25, 45 or 60 mols ethylene oxide);

monostearyl mono(polyethoxy) amyl methyl quaternary ammonium chloride, iodide, bromide, sulfonate and sulfate (with 5, 15, 25, 45 or 60 mols ethylene oxide);

monotallow mono(polyethoxy) amyl methyl quaternary ammonium chloride, iodide, bromide, sulfonate and sulfate (with 5, 15, 25, 45 or 60 mols ethylene oxide);

monolauryl mono(polyethoxy) amyl methyl quaternary ammonium chloride, iodide, bromide, sulfonate and sulfate (with 5, 15, 25, 45 or 60 mols ethylene oxide);

monococo mono(polyethoxy) amyl methyl quaternary ammonium chloride, iodide, bromide, sulfonate and sulfate (with 5, 15, 25, 45 or 60 mols ethylene oxide);

monomyristyl mono(polyethoxy) amyl methyl quaternary ammonium chloride, iodide, bromide, sulfonate and sulfate (with 5, 15, 25, 45 or 60 mols ethylene oxide);

monobehenyl mono(polyethoxy) amyl methyl quaternary ammonium chloride, iodide, bromide, sulfonate and sulfate (with 5, 15, 25, 45 or 60 mols ethylene oxide);

monopalmityl mono(polyethoxy) amyl methyl quaternary ammonium chloride, iodide, bromide, sulfonate and sulfate (with 5, 15, 25, 45 or 60 mols ethylene oxide);

monosoya mono(polyethoxy) amyl methyl quaternary ammonium chloride, iodide, bromide, sulfonate and sulfate (with 5, 15, 25, 45 or 60 mols ethylene oxide);

monooleyl mono(polyethoxy) amyl methyl quaternary ammonium chloride, iodide, bromide, sulfonate and sulfate (with 5, 15, 25, 45 or 60 mols ethylene oxide);

monostearyl mono(polyethoxy) hexyl methyl quaternary ammonium chloride, iodide, bromide, sulfonate and sulfate (with 5, 15, 25, 45 or 60 mols ethylene oxide);

monotallow mono(polyethoxy) hexyl methyl quaternary ammonium chloride, iodide, bromide, sulfonate and sulfate (with 5, 15, 25, 45 or 60 mols ethylene oxide);

monolauryl mono(polyethoxy) hexyl methyl quaternary ammonium chloride, iodide, bromide, sulfonate and sulfate (with 5, 15, 25, 45 or 60 mols ethylene oxide);

monococo mono(polyethoxy) hexyl methyl quaternary ammonium chloride, iodide, bromide, sulfonate and sulfate (with 5, 15, 25, 45 or 60 mols ethylene oxide);

monomyristyl mono(polyethoxy) hexyl methyl quaternary ammonium chloride, iodide, bromide, sulfonate and sulfate (with 5, 15, 25, 45 or 60 mols ethylene oxide);

monobehenyl mono(polyethoxy) hexyl methyl quaternary ammonium chloride, iodide, bromide, sulfonate and sulfate (with 5, 15, 25, 45 or 60 mols ethylene oxide);

monopalmityl mono(polyethoxy) hexyl methyl quaternary ammonium chloride, iodide, bromide, sulfonate and sulfate (with 5, 15, 25, 45 or 60 mols ethylene oxide);

monosoya mono(polyethoxy) hexyl methyl quaternary ammonium chloride, iodide, bromide, sulfonate and sulfate (with 5, 15, 25, 45 or 60 mols ethylene oxide);

monooleyl mono(polyethoxy) hexyl methyl quaternary ammonium chloride, iodide, bromide, sulfonate and sulfate (with 5, 15, 25, 45 or 60 mols ethylene oxide);

monostearyl mono(polyethoxy) benzyl methyl quaternary ammonium chloride, iodide, bromide, sulfonate and sulfate (with 5, 15, 25, 45 or 60 mols ethylene oxide);

monotallow mono(polyethoxy) benzyl methyl quaternary ammonium chloride, iodide, bromide, sulfonate and sulfate (with 5, 15, 25, 45 or 60 mols ethylene oxide);

monolauryl mono(polyethoxy) benzyl methyl quaternary ammonium chloride, iodide, bromide, sulfonate and sulfate (with 5, 15, 25, 45 or 60 mols ethylene oxide);

monococo mono(polyethoxy) benzyl methyl quaternary ammonium chloride, iodide, bromide, sulfonate and sulfate (with 5, 15, 25, 45 or 60 mols ethylene oxide);

monostearyl mono(polypropoxy) methyl methyl quaternary ammonium chloride, bromide, sulfonate and sulfate (with 5, 15, 25, 45 or 60 mols propylene oxide);

monotallow mono(polypropoxy)methyl methyl quaternary ammonium chloride, bromide, sulfonate and sulfate (with 5, 15, 25, 45 or 60 mols propylene oxide);

monolauryl mono(polypropoxy) methyl methyl quaternary ammonium chloride, bromide, sulfonate and sulfate (with 5, 15, 25, 45 or 60 mols propylene oxide);

monococo mono(polypropoxy) methyl methyl quaternary ammonium chloride, iodide, bromide, sulfonate and sulfate (with 5, 15, 25, 45 or 60 mols propylene oxide);

monomyristyl mono(polypropoxy) methyl methyl quaternary ammonium chloride, iodide, bromide, sulfonate and sulfate (with 5, 15, 25, 45 or 60 mols propylene oxide);

monobehenyl mono(polypropoxy) methyl methyl quaternary ammonium chloride, iodide, bromide, sulfonate and sulfate (with 5, 15, 25, 45 or 60 mols propylene oxide);
monopalmityl mono(polypropoxy) methyl methyl quaternary ammonium chloride, iodide, bromide, sulfonate and sulfate (with 5, 15, 25, 45, or 60 mols propyleneoxide);
monosoya mono(polypropoxy) methyl methyl quaternary ammonium chloride, iodide, bromide, sulfonate and sulfate (with 5, 15, 25, 45 or 60 mols propyleneoxide);
monooleyl mono(polypropoxy) methyl methyl quaternary ammonium chloride, iodide, bromide, sulfonate and sulfate (with 5, 15, 25, 45 or 60 mols propylene oxide);
monostearyl mono(polypropoxy) ethyl methyl quaternary ammonium chloride, iodide, bromide, sulfonate and sulfate (with 5, 15, 25, 45 or 60 mols propylene oxide);
monotallow mono(polypropoxy) ethyl methyl quaternary ammonium chloride, iodide, bromide, sulfonate and sulfate (with 5, 15, 25, 45 or 60 mols propylene oxide);
monolauryl mono(polypropoxy) ethyl methyl quaternary ammonium chloride, iodide, bromide, sulfonate and sulfate (with 5, 15, 25, 45 or 60 mols propylene oxide);
monococo mono(polypropoxy) ethyl methyl quaternary ammonium chloride, iodide, bromide, sulfonate and sulfate (with 5, 15, 25, 45 or 60 mols propylene oxide);
monomyristyl mono(polypropoxy) ethyl methyl quaternary ammonium chloride, iodide, bromide, sulfonate and sulfate (with 5, 15, 25, 45 or 60 mols propylene oxide);
monobehenyl mono(polypropoxy) ethyl methyl quaternary ammonium chloride, iodide, bromide, sulfonate and sulfate (with 5, 15, 25, 45 or 60 mols propylene oxide);
monobehenyl mono(polypropoxy) ethyl methyl quaternary ammonium chloride, iodide, bromide, sulfonate and sulfate (with 5, 15, 25, 45 or 60 mols propylene oxide);
monosoya mono(polypropoxy) ethyl methyl quaternary ammonium chloride, iodide, bromide, sulfonate and sulfate (with 5, 15, 25, 45 or 60 mols propylene oxide);
monooleyl mono(polypropoxy) ethyl methyl quaternary ammonium chloride, iodide, bromide, sulfonate and sulfate (with 5, 15, 25, 45 or 60 mols propylene oxide);
monostearyl mono(polypropoxy) propyl methyl quaternary ammonium chloride, iodide, bromide, sulfonate and sulfate (with 5, 15, 25, 45 or 60 mols propylene oxide);
monotallow mono(polypropoxy) propyl methyl quaternary ammonium chloride, iodide, bromide, sulfonate and sulfate (with 5, 15, 25, 45 or 60 mols propylene oxide);
monolauryl mono(polypropoxy) propyl methyl quaternary ammonium chloride, iodide, bromide, sulfonate and sulfate (with 5, 15, 25, 45 or 60 mols propylene oxide);
monococo mono(polypropoxy) propyl methyl quaternary ammonium chloride, iodide, bromide, sulfonate and sulfate (with 5, 15, 25, 45 or 60 mols propylene oxide);
monomyristyl mono(polypropoxy) propyl methyl quaternary ammonium chloride, iodide, bromide, sulfonate and sulfate (with 5, 15, 25, 45 or 60 mols propylene oxide);
monobehenyl mono(polypropoxy) propyl methyl quaternary ammonium chloride, iodide, bromide, sulfonate and sulfate (with 5, 15, 25, 45 or 60 mols propylene oxide);
monopalmityl mono(polypropoxy) propyl methyl quaternary ammonium chloride, iodide, bromide, sulfonate and sulfate (with 5, 15, 25, 45 or 60 mols propylene oxide);
monosoya mono(polypropoxy) propyl methyl quaternary ammonium chloride, iodide, bromide, sulfonate and sulfate (with 5, 15, 25, 45 or 60 mols propylene oxide);
monooleyl mono(polypropoxy) propyl methyl quaternary ammonium chloride, iodide, bromide, sulfonate and sulfate (with 5, 15, 25, 45 or 60 mols propylene oxide);
monostearyl mono(polypropoxy) n-butyl methyl quaternary ammonium chloride, iodide, bromide, sulfonate and sulfate (with 5, 15, 25, 45 or 60 mols propylene oxide);
monotallow mono(polypropoxy) n-butyl methyl quaternary ammonium chloride, iodide, bromide, sulfonate and sulfate (with 5, 15 25, 45 or 60 mols propylene oxide);
monolauryl mono(polypropoxy) n-butyl methyl quaternary ammonium chloride, iodide, bromide, sulfonate and sulfate (with 5, 15, 25, 45 or 60 mols propylene oxide);
monococo mono(polypropoxy) n-butyl methyl quaternary ammonium chloride, iodide, bromide, sulfonate and sulfate (with 5, 15, 25, 45 or 60 mols propylene oxide);
monomyristyl mono(polypropoxy) n-butyl methyl quaternary ammonium chloride, iodide, bromide, sulfonate and sulfate (with 5, 15, 25, 45 or 60 mols propylene oxide);
monobehenyl mono(polypropoxy) n-butyl methyl quaternary ammonium chloride, iodide, bromide, sulfonate and sulfate (with 5, 15, 25, 45 or 60 mols propylene oxide);
monopalmityl mono(polypropoxy) n-butyl methyl quaternary ammonium chloride, iodide, bromide, sulfonate and sulfate (with 5, 15, 25, 45 or 60 mols propylene oxide);
monosoya mono(polypropoxy) n-butyl methyl quaternary ammonium chloride, iodide, bromide, sulfonate and sulfate (with 5, 15, 25 45 or 60 mols propylene oxide);
monooleyl mono(polypropoxy( n-butyl methyl quaternary ammonium chloride, iodide, bromide, sulfonate and sulfate (with 5, 15, 25, 45 or 60 mols propylene oxide);
monostearyl mono(polypropoxy) secondary butyl methyl quaternary ammonium chloride, iodide, bromide, sulfonate and sulfate (with 5, 15, 25, 45 or 60 mols propylene oxide);
monotallow mono(polypropoxy) secondary butyl methyl quaternary ammonium chloride, iodide, bromide, sulfonate and sulfate (with 5, 15, 25, 45 or 60 mols propylene oxide);
monolauryl mono(polypropoxy) secondary butyl methyl quaternary ammonium chloride, iodide, bromide, sulfonate and sulfate (with 5, 15, 25, 45 or 60 mols propylene oxide);
monococo mono(polypropoxy) secondary butyl methyl quaternary ammonium chloride, iodide, bromide, sulfonate and sulfate (with 5, 15, 25 45 or 60 mols propylene oxide);

monomyristyl mon(polypropoxy) secondary butyl methyl quaternary ammonium chloride, iodide, bromide, sulfonate and sulfate (with 5, 15, 25, 45 or 60 mols propylene oxide);

monobehenyl mono(polypropoxy) secondary butyl methyl quaternary ammonium chloride, iodide, bromide, sulfonate and sulfate (with 5, 15, 25, 45 or 60 mols propylene oxide);

monopalmityl mon(polypropoxy) secondary butyl methyl quaternary ammonium chloride, iodide, bromide, sulfonate and sulfate (with 5, 15, 25, 45 or 60 mols propylene oxide);

monosoya mono(polypropoxy) secondary butyl methyl quaternary ammonium chloride, iodide, bromide, sulfonate and sulfate (with 5, 15, 25, 45 or 60 mols propylene oxide);

monooleyl mono(polypropoxy) secondary butyl methyl quaternary ammonium chloride, iodide, bromide, sulfonate and sulfate (with 5, 15, 25, 45 or 60 mols propylene oxide);

monostearyl mono(polypropoxy) amyl methyl quaternary ammonium chloride, iodide, bromide, sulfonate and sulfate (with 5, 15, 25, 45 or 60 mols propylene oxide);

monotallow mono(polypropoxy) amyl methyl quaternary ammonium chloride, iodide, bromide, sulfonate and sulfate (with 5, 15, 25, 45 or 60 mols propylene oxide);

monolauryl mono(polypropoxy) amyl methyl quaternary ammonium chloride, iodide, bromide, sulfonate and sulfate (with 5, 15, 25, 45 or 60 mols propylene oxide);

monococo mono(polypropoxy) amyl methyl quaternary ammonium chloride, iodide, bromide, sulfonate and sulfate (with 5, 15, 25, 45 or 60 mols propylene oxide);

monomyristyl mono(polypropoxy) amyl methyl quaternary ammonium chloride, iodide, bromide, sulfonate and sulfate (with 5, 15, 25, 45 or 60 mols propylene oxide);

monobehenyl mono(polypropoxy) amyl methyl quaternary ammonium chloride, iodide, bromide, sulfonate and sulfate (with 5, 15, 25, 45 or 60 mols propylene oxide);

monopalmityl mono(polypropoxy) amyl methyl quaternary ammonium chloride, iodide, bromide, sulfonate and sulfate (with 5, 15, 25, 45 or 60 mols propylene oxide);

monosoya mono(polypropoxy) amylmethyl quaternary ammonium chloride, iodide, bromide sulfonate and sulfate (with 5, 15, 25, 45 or 60 mols propylene oxide);

monooleyl mono(polypropoxy) amyl methyl quaternary ammonium chloride, iodide, bromide, sulfonate and sulfate (with 5, 15, 25, 45 or 60 mols propylene oxide);

monostearyl mono(polypropoxy) hexyl methyl quaternary ammonium chloride, iodide, bromide, sulfonate and sulfate (with 5, 15, 25, 45 or 60 mols propylene oxide);

monotallow mono(polypropoxy) hexyl methyl quaternary ammonium chloride iodide, bromide, sulfonate and sulfate (with 5, 15, 25, 45 or 60 mols propylene oxide);

monolauryl mono(polypropoxy) hexyl methyl quaternary ammonium chloride, iodide, bromide, sulfonate and sulfate (with 5, 15, 25, 45 or 60 mols propylene oxide);

monococo mono(polypropoxy) hexyl methyl quaternary ammonium chloride, iodide, bromide, sulfonate and sulfate (with 5, 15 25, 45 or 60 mols propylene oxide);

monomyristyl mono(polypropoxy) hexyl methyl quaternary ammonium chloride, iodide, bromide, sulfonate and sulfate (with 5, 15, 25, 45 or 60 mols propylene oxide);

monobehenyl mono(polypropoxy) hexyl methyl quaternary ammonium chloride, iodide, bromide, sulfonate and sulfate (with 5, 15, 25, 45 or 60 mols propylene oxide);

monopalmityl mono(polypropoxy) hexyl methyl quaternary ammonium chloride, iodide, bromide, sulfonate and sulfate (with 5, 15, 25, 45 or 60 mols propylene oxide);

monosoya mono(polypropoxy) hexyl methyl quaternary ammonium chloride, iodide, bromide, sulfonate and sulfate (with 5, 15, 25, 45 or 60 mols propylene oxide);

monooleyl mono(polypropoxy) hexyl methyl quaternary ammonium chloride, iodide, bromide, sulfonate and sulfate (with 5, 15, 25, 45 or 60 mols propylene oxide);

monostearyl mono(polypropoxy) benzyl methyl quaternary ammonium chloride, iodide, bromide, sulfonate and sulfate (with 5, 15, 25, 45 or 60 mols propylene oxide);

monotallow mono(polypropoxy) benzyl methyl quaternary ammonium chloride, iodide, bromide, sulfonate and sulfate (with 5, 15, 25, 45 or 60 mols propylene oxide);

monolauryl mono(polypropoxy) benzyl methyl quaternary ammonium chloride, iodide, bromide, sulfonate and sulfate (with 5, 15, 25, 45 or 60 mols propylene oxide);

monococo mono(polypropoxy) benzyl methyl quaternary ammonium chloride, iodide, bromide, sulfonate and sulfate (with 5, 15, 25, 45 or 60 mols propylene oxide);

monomyristyl mono(polyethoxy) benzyl methyl quaternary ammonium chloride, iodide, bromide, sulfonate and sulfate (with 5, 15, 25, 45 or 60 mols ethylene oxide);

monobehenyl mono(polyethoxy) benzyl methyl quaternary ammonium chloride, iodide, bromide, sulfonate and sulfate (with 5, 15, 25, 45 or 60 mols ethylene oxide);

monopalmityl mono(polyethoxy) benzyl methyl quaternary ammonium chloride, iodide, bromide, sulfonate and sulfate (with 5, 15, 25, 45 or 60 mols ethylene oxide);

monosoya mono(polyethoxy) benzyl methyl quaternary ammonium chloride, iodide, bromide, sulfonate and sulfate (with 5, 15, 25, 45 or 60 mols ethylene oxide);

monooleyl mono(polyethoxy) benzyl methyl quaternary ammonium chloride, iodide, bromide, sulfonate and sulfate (with 5, 15, 25, 45 or 60 mols ethylene oxide);

Commercial tallow, soya and coco amines are used in the production of compounds of the instant invention. As is well known commercial tallow amine contains about 75% of stearyl and palmityl, and 25% of oleyl. A commercial soya amine contains about 52% of linoyl, 33% of oleyl, 7% of stearyl and palmityl and 8% of hexyl, octyl and decyl and a commercial coco contains about 40% lauryl, 15% myristyl, 15% oleyl and stearyl, and the balance hexyl, octyl and decyl.

There now will be pointed out a method pursuant to which quaternary ammonium polyalkoxy alkyl alkyl salts such as described above can be used in an aqueous composition for the relief of rectal itching, and the lessening of irritation and swelling of prolapsed and of irritated and swollen hemorrhoids by topical application to the affected areas.

The quaternary ammonium polyalkoxy alkyl alkyl salts of the invention are diluted in water, with which they are not reactive, to form a composition. The amount of the active ingredient, to wit, the quaternary ammonium polyalkoxy alkyl alkyl salts of the invention, can be varied very widely. For example, as little as 0.01% by weight to as much as 50% by weight of the quaternary ammonium salt of the invention in a water solution will relieve symptoms of the character under consideration.

One specific composition is the combination of a quaternary ammonium polyalkoxy alkyl alkyl salt of the invention and water. The percentage by weight of the quaternary ammonium salt incorporated in the water may vary from as little as 0.01% by weight to approximately 10% by weight. In these proportions the composition is watery. Good results are obtained with a concentration of about 0.03% by weight in water in a bathtub and of about 0.1% by weight in water in a sitz bath, in either of which the afflicted patient sits with the affected areas exposed to the composition.

Another method using a water solution of the quaternary ammonium salts of the invention is to provide a composition in the form of a concentrate, e.g. a 25% by weight water solution of a quaternary ammonium salt of the invention, and then to disperse 1 to 2 ounces of the concentrate in a bathtub full of water, e.g. about 14 gallons. With one ounce of such concentrate the concentration of the quaternary ammonium salt is approximately 0.05% by weight and with two ounces about 0.1% by weight. It has been found that excellent results are obtained where the quaternary ammonium salts of the invention are present in a bathtub full of water in a range of from about 0.01% to 0.5% by weight.

An excellent regime followed for water immersions, either in a bathtub or in a sitz bath (this regime is merely exemplificative, inasmuch as any regime is acceptable where the affected parts have a quaternary ammonium salt of the invention applied thereto in water in any concentration indicated) is to immerse the affected part in a bathtub or stiz bath containing a water solution of quaternary ammonium salts of the invention in the dilution range mentioned above.

AS a matter of general hygiene in any regime using a quaternary ammonium salt of the invention, the patients are instructed to use cotton and warm water instead of toilet tissue after defecation. The patients bathe 1 to 3 times a day in a water bath containing a quaternary ammonium salt of the invention, e.g. a bathtub full of water or a stiz bath within the concentration range indicted. It should be noted that the high end of the range of the compositions indicated are not advantageously exceeded, because at the high end good results are obtained which are not made noticeably better by increasing the concentration. The bathtub or the sitz bath is maintained at a temperature of about 110°F during immersion. Preferably, such a bath, either in a bathtub or in a sitz bath, is taken before retiring, and additional baths, if the severity of the affliction warrants, are taken once or twice during the day, e.g. once on arising and once more at mid-day. The duration of the immersion is about fifteen to twenty minutes. The longer the immersion, the better the results. However, even short periods of immersion, e.g. five minutes, have been found to be useful. Noticeably good results usually are obtained in about one week, although if the condition is severe, longer periods of treatment are indicated, e.g. as much as 12 weeks.

In describing the water-based compositions containing the quaternary ammonium salts of the invention over a wide range of percentages such as indicated, it is to be understood that good results are obtained with the complete spectrum of quaternary ammonium salts listed above, and that the specific examples of weight proportions mentioned are applicable to each and every one of said quaternary ammonium salts, so that the following example of a use of the invention is only by way of illustration, and it is to be understood that the particular quaternary ammonium salt mentioned in this example can be substituted by any one of the other quaternary ammonium salts of the invention, and that symptomatic relief will be obtained with all of them.

EXAMPLE I

A concentrate is prepared by mixing 25% by weight of monotallow bis(polyethoxy) (25mols ethylene oxide) monoethyl ammonium sulfate in water, i.e. 25 grams of said quaternary ammonium salt and 75 cc of water. As noted above, the same concentration will be useful if any other of the aforesaid quaternary ammonium polyalkoxy alkyl alkyl salts are employed. Any of these concentrates is added to a fourteen-gallon bathtub of water and used at the temperature above described.

EXAMPLE II

The above concentrate is added to one gallon of water to make a stiz bath which is used for 10 to 15 minutes at the temperature above described.

Another composition useful in the practice of the invention is the combination of an aforesaid quaternary ammonium salt of the invention and water wherein the amount of the said salt is from about 25% to about 40% by weight of the composition. Such a composition of the said salt with water is still somewhat watery and is employed in the practice of the invention by applying the same to affected areas with a cotton swab. The same hygienic regime as noted above with respect to immersion in a bathtub or in a sitz bath is followed with respect to rectal irrigation, topical rectal cleansing and frequency of and times of the day for application. Between the 10% figure and the 25% figure the mode of application can be either by immersion or by cotton swab.

At higher concentrations (above 25%) the composition applied with a swab or by finger-smearing will tend to remain in the area because it has either an oily or creamy consistency. If it is desired to prevent staining of clothes and to prolong treatment, the composition after application may be protected with a gauze pad.

It is to be specifically observed that the compositions above recited are to be used for topical application in humans for the relief of rectal itching and lessening of irritation and swelling of prolapsed and of irritated and swollen external hemorrhoids.

Having thus described the invention, there is claimed as new and desired to be secured by Letters Patent:

1. A method of treating external hemorrhoids in humans by relieving rectal itching and lessening of irritation and swelling of prolapsed and of irritated and swollen hemorrhoids, said method comprising immersing the affected area in a water bath containing as the active ingredient thereof from 0.01 to 0.5% by weight of a compound selected from the group consisting of

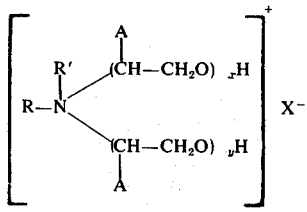

where R is a saturated or unsaturated fatty alkyl having from 10 to 25 carbon atoms, each A is hydrogen or methyl, R' is a lower alkyl having from 1 to 6 carbon atoms, $x$ is at least 2, $y$ is at least 2, $x + y$ are from 5 to 60 and X is selected from the group consisting of chlorides, iodides, bromides, sulfonates and sulfates,

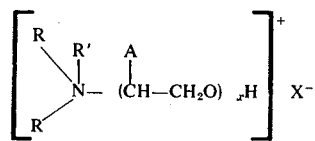

where each R is a saturated or unsaturated fatty alkyl having from 10 to 25 carbon atoms, A is hydrogen or methyl, R' is a lower alkyl having from 1 to 6 carbon atoms, $x$ is from 5 to 60 and X is selected from the group consisting of chlorides, iodides, bromides, sulfonates and sulfates, and

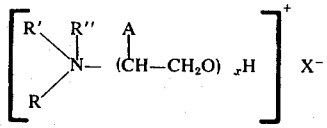

where R is a saturated or unsaturated fatty alkyl having from 10 to 25 carbon aroms, A is hydrogen, or methyl, R' and R'' are each a lower alkyl having from 1 to 6 carbon atoms, $x$ is from 5 to 60 and X is selected from the group consisting of chlorides, iodides, bromides, sulfonates, and sulfates.

2. A method as set forth in claim 1 wherein the immersion of the affected area is from about 5 to 20 minutes and is repeated daily for a period of from about 1 to about 12 weeks.

* * * * *